(12) United States Patent
Delahanty et al.

(10) Patent No.: US 12,037,568 B2
(45) Date of Patent: Jul. 16, 2024

(54) SEMICONDUCTOR CELL CULTURE DEVICE AND A SYSTEM FOR THREE-DIMENSIONAL CELL CULTURE

(71) Applicants: IMEC VZW, Leuven (BE); Katholieke Universiteit Leuven, Leuven (BE)

(72) Inventors: Aaron Delahanty, Leuven (BE); Dries Braeken, Leuven (BE); Alexandru Andrei, Wolluwe Saint Pierre (BE); Peter Peumans, Herfelingen (BE); Carolina Mora Lopez, Kessel-Lo (BE); Veerle Reumers, Putte (BE); Veronique Rochus, Embourg (BE); Bart Weekers, Leuven (BE)

(73) Assignees: IMEC VZW, Leuven (BE); Katholieke Universiteit Leuven, Leuven (BE)

( * ) Notice: Subject to any disclaimer, the term of this patent is extended or adjusted under 35 U.S.C. 154(b) by 823 days.

(21) Appl. No.: 17/128,091

(22) Filed: Dec. 19, 2020

(65) Prior Publication Data

US 2021/0189310 A1    Jun. 24, 2021

(30) Foreign Application Priority Data

Dec. 20, 2019 (EP) ..................................... 19218559

(51) Int. Cl.
*C12M 1/34* (2006.01)
*C12N 1/00* (2006.01)

(52) U.S. Cl.
CPC ................. *C12M 1/34* (2013.01); *C12N 1/00* (2013.01); *C12N 2513/00* (2013.01)

(58) Field of Classification Search
CPC ........ C12M 1/34; C12M 23/58; C12M 25/14; C12M 35/02; C12N 1/00; C12N 2513/00
See application file for complete search history.

(56) References Cited

U.S. PATENT DOCUMENTS 9,457,128 B2   10/2016   Lieber et al.
2006/0265039 A1   11/2006   Bartic et al.
(Continued)

FOREIGN PATENT DOCUMENTS

WO   WO-2019/050947 A1   3/2019

OTHER PUBLICATIONS

Huang et al., "Stretchable silicon sensor networks for structural health monitoring", Proceedings SPIE 6174, Smart Structures and Materials: Sensors and Smart Structures Technologies for Civil, Mechanical, and Aerospace Systems, 617412, Apr. 11, 2006.
(Continued)

*Primary Examiner* — Michael L Hobbs
(74) *Attorney, Agent, or Firm* — MOSER TABOADA

(57) ABSTRACT

A semiconductor cell culture device for three-dimensional cell culture comprises: a semiconductor material layer in which a cell culture portion of semiconductor material is defined, wherein the cell culture portion defines an area within the semiconductor material layer surrounded by semiconductor material, wherein the cell culture portion comprises a mesh structure having island structures being interconnected by bridge structures and defining through-pores between the island structures allowing for selective transport of cell constructs, cellular components, proteins or other large molecules through the semiconductor material layer and on opposite sides of the cell culture portion in the semiconductor material layer, and a supporting structure connected to the cell culture portion.

18 Claims, 7 Drawing Sheets

(56) References Cited

U.S. PATENT DOCUMENTS

2010/0143848 A1* 6/2010 Jain .................. B23K 26/40
  430/311
2010/0207487 A1 8/2010 Carralero et al.
2014/0074253 A1* 3/2014 Lieber .................. C12M 35/02
  435/395

OTHER PUBLICATIONS

Park et al., "Microfluidic compartmentalized co-culture platform for CNS axon myelination research", Biomed Microdevices, vol. 11, No. 6, pp. 1145-1153, Dec. 2009.
Hussain et al., "CMOS-Technology-Enabled Flexible and Stretchable Electronics for Internet of Everything Applications", Advanced Materials, vol. 28, pp. 4219-4249, 2016.
Extended European Search Report for Application No. EP 19218559.3, dated Jun. 16, 2020.

* cited by examiner

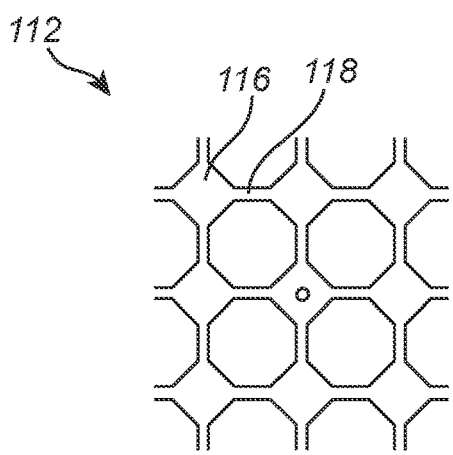 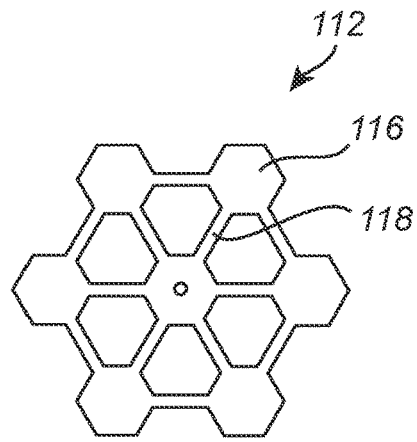
FIG. 3A  FIG. 3B
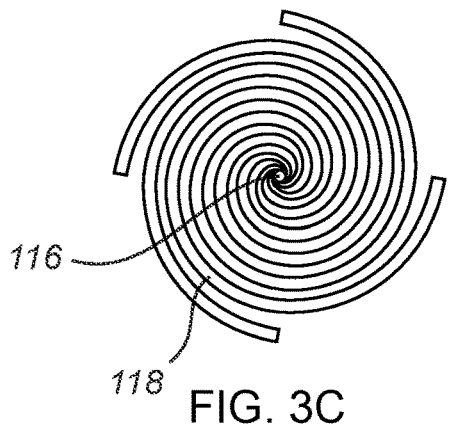 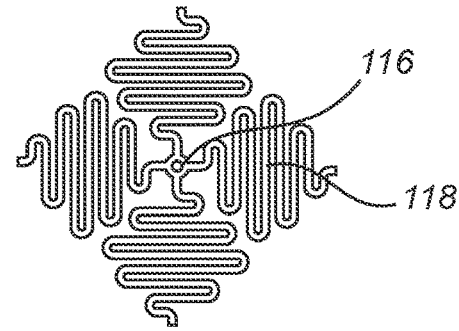
FIG. 3C  FIG. 3D
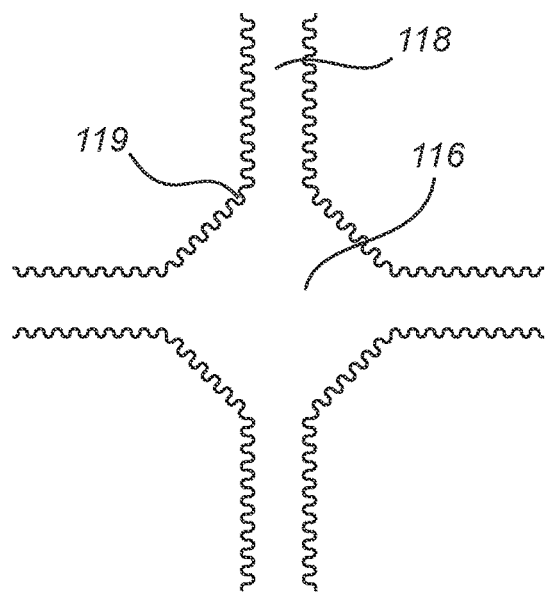
FIG. 4

SEMICONDUCTOR CELL CULTURE DEVICE AND A SYSTEM FOR THREE-DIMENSIONAL CELL CULTURE

CROSS-REFERENCE TO RELATED APPLICATIONS

The present application is based on priority claimed on European Patent Application No. 19218559.3, filed on Dec. 20, 2019, the contents of which are incorporated herein by reference.

TECHNICAL FIELD

The present inventive concept relates to a semiconductor cell culture device, which may or may not be used for analysis and/or actuation of a three-dimensional cell culture.

BACKGROUND

Culturing of three-dimensional cell constructs is of high interest, since it may enable studying of three-dimensional structures that mimic structures found in living organisms, such as mimicking brain structures. This may be useful e.g. for neuroscience research.

However, three-dimensional cell and tissue constructs may not allow for making measurements, such as recording electrical signals or potentials, in interior parts within the three-dimensional structure. Further, some constructs may also require nutrient delivery throughout the construct, and this may be difficult to provide.

SUMMARY

It is an object of the present inventive concept to provide a cell culture device which may facilitate culturing of three-dimensional cell cultures. It is a particular object of the present inventive concept to provide a cell culture device which may allow for making measurements interior to a three-dimensional cell culture.

These and other objects of the invention are at least partly met by the invention as defined in the independent claims. Preferred embodiments are set out in the dependent claims.

According to a first aspect, there is provided a semiconductor cell culture device for three-dimensional cell culture, said device comprising: a semiconductor material layer in which a cell culture portion of semiconductor material is defined, wherein the cell culture portion defines an area within the semiconductor material layer surrounded by semiconductor material, wherein the cell culture portion comprises a mesh structure having island structures being interconnected by bridge structures and defining through-pores between the island structures allowing for selective transport of cell constructs, cellular components, proteins or other large molecules through the semiconductor material layer and on opposite sides of the cell culture portion in the semiconductor material layer, and a supporting structure connected to the cell culture portion.

Thanks to the through-pores being provided in the mesh structure, a through flow is provided through the mesh structure. This through flow may allow cell constructs to be formed to extend through the mesh structure and, thus, be arranged on opposite sides of the cell culture portion. Hence, the island structures and bridge structures may be formed within a cell culture and extend into the interior of a three-dimensional cell culture. This may be used for analysis of interior portions of the three-dimensional cell culture.

However, the semiconductor cell culture device need not necessarily be used for analysis of the three-dimensional cell culture. Even though a semiconductor structure is suitable for providing electronic circuitry thereon, the semiconductor cell culture device can be used merely to define a structure for cell culture. The semiconductor structure may be used for defining a geometry that may stimulate a particular cell culture for controlling the cell culture. For instance, the size of through-pores may control the cell culture. The semiconductor cell structure device may also in some embodiments be configured such that the mesh structure assumes a desired shape in three dimensions, which may stimulate forming of a desired three-dimensional shape of a cell construct. In this case, it is possible to utilize strains within the mesh structure that may be created in the island structures and bridge structures, such that the strains may force a planar semiconductor material layer in which the mesh structure is created to transform into a desired shape.

Thanks to the use of a semiconductor material, such as silicon, the forming of the mesh structure may be easily controlled for defining a small structure with desired geometry. Using conventional semiconductor manufacturing technology, it is possible to define minute structures in a very accurate manner. Thus, the cell culture portion being formed in a semiconductor material layer enables accurate manufacture of desired shapes and sizes of structures within the cell culture portion. The size and shape of parts of the mesh structure may thus be accurately controlled by the mesh structure being formed in a semiconductor material layer.

The through flow may allow for selective transport of cell constructs, cellular components, proteins or other large molecules through the semiconductor material layer. Thus, a size of the through-pores may control the selective transport. The through-pores may be sufficiently large to allow cell bodies to pass therethrough. However, in some embodiments, the through-pores may have a size of approximately 5 μm or approximately 2.5 μm or therebetween, which may allow neurites to pass through the through-pores but prevent cell bodies to pass therethrough. In such case, the through-pores may be used for allowing transport of components through the mesh structure so as to facilitate nutrient delivery through the mesh structure even though cell constructs may not necessarily be grown through the mesh structure.

The cell culture portion may be defined in a semiconductor material layer. This implies that the cell culture portion may, during manufacture, be formed in a planar layer. For instance, the cell culture portion may be formed in a semiconductor substrate, such as a silicon wafer. The cell culture portion may thus extend in a plane. However, the cell culture portion need not necessarily extend in a plane in the semiconductor cell culture device. Rather, the semiconductor material layer may assume a three-dimensional shape such that the cell culture portion extends in three dimensions, e.g. a helical shape, which may be useful in controlling a desired shape of a cell construct.

The cell culture portion defines an area in the semiconductor material layer. Thus, the cell culture portion is surrounded by semiconductor material. Hence, the cell culture portion may define through-pores as the only connections between opposite sides of the cell culture portion. This is advantageous in controlling culture of cell constructs on opposite sides and/or through the cell culture portion.

The supporting structure may be configured to provide support on opposite sides of the area of the cell culture portion, i.e. at opposite sides of a periphery of the cell culture portion in the semiconductor material layer. This may be useful when the cell culture portion is extending in a plane, whereby the supporting structure may provide stability to ensure that the cell culture portion is maintained in the plane. Also, the supporting structure may be thicker than the cell culture portion, which may be used for creating a space between the cell culture portion and another structure, for example another cell culture portion on another semiconductor cell culture device when such devices are stacked.

However, it should be realized that the supporting structure may alternatively be provided on only one side of the area of the cell culture portion. For instance, a portion of the semiconductor material layer with the cell culture portion may extend as a cantilever structure from the supporting structure.

The supporting structure may be formed in the semiconductor material layer for being connected to the cell culture portion. For instance, the supporting structure may be a portion of the semiconductor material layer that may or may not have a larger thickness than the cell culture portion in the semiconductor material layer. Alternatively or additionally, the supporting structure may comprise a structure that is attached to a portion of the semiconductor material layer for connecting the supporting structure to the cell culture portion.

The semiconductor cell culture device may be used for probing into a three-dimensional cell culture. For instance, the supporting structure may be arranged external to the cell culture with the cell culture portion extending from the supporting structure in a cantilever-type arrangement. The cell culture may then extend on opposite sides of the cell culture portion and may further extend around an end of the semiconductor material layer in which the cell culture portion is defined.

The semiconductor cell culture device may alternatively be arranged with supporting structures on opposite sides of a three-dimensional cell culture. This may be particularly useful if the semiconductor cell culture device is to be stacked so as to provide two or more cell culture portions extending e.g. in parallel planes through a cell culture.

As used herein, a "cell construct" should be understood as any cell or combination of cells that may form a three-dimensional shape.

It should be realized that the cell culture portion being defined in the semiconductor material layer may also extend in one or more additional layers above or below the semiconductor material layer. Thus, for instance if an electronic circuitry is defined in the mesh structure, additional dielectric layer(s) may be provided on the semiconductor material layer for providing e.g. metal structures on the dielectric layer(s). Thus, the through-pores may extend through both the semiconductor material layer as well as other layers.

According to an embodiment, the semiconductor cell culture device further comprises a plurality of sensors for analysis of a cell construct, wherein each of the plurality of sensors is arranged on an island structure and wherein sensor connections to the plurality of sensors are arranged on the bridge structures.

The semiconductor cell culture device provides island structures which are able to extend into the interior of a three-dimensional cell culture. By having sensors arranged on the island structures, the semiconductor cell culture device enables performing measurements and thereby analyzing the interior of a cell construct.

Thanks to the use of a semiconductor material layer in forming the cell culture portion, the cell culture device facilitates arranging sensors on island structures and providing connections to such sensors for control and read-out of measurements.

According to an embodiment, the plurality of sensors comprises at least one of: an electrode for detecting an electrical signal, a photosensitive area for detecting light or a piezoelectric sensor.

Sensors may be used in various ways for detecting different properties of a cell construct. The semiconductor cell culture device may comprise sensors of one or more types. Having sensors of different types may enable acquiring of various information relating to the cell construct. Having sensors of only a single type may reduce complexity of circuitry in the semiconductor cell culture device.

The sensors may include electrodes for detecting electrical signals. Thus, electrical signals propagating in the three-dimensional cell culture, spontaneously or as a response to stimulation, may be recorded.

The sensors may include photosensitive areas. This may be used for imaging an interior of the cell construct.

The sensors may include a piezoelectric sensor. This may be used for detecting e.g. changes in pressure, temperature or strain within the cell construct.

According to an embodiment, the semiconductor cell culture device further comprises a plurality of actuators for affecting a cell construct, wherein each of the plurality of actuators is arranged on an island structure and wherein actuator connections to the plurality of actuators are arranged on the bridge structures.

Actuators may be used for affecting the cell construct, such as for triggering a response from the cell construct that may be measured. Thus, actuators may for example include electrodes for providing a stimulation signal to the cell construct, whereby a response to the stimulation signal may be recorded.

The actuators may alternatively comprise light-emitting diodes or other light sources for illuminating the cell construct e.g. for imaging and/or for providing excitation light that may induce emission of light from the cell construct. A light source may be provided on an island structure. However, according to an alternative, the light source may be external to the cell culture portion and light may be guided through waveguides to the island structures, wherein light is emitted towards the cell construct.

The actuators may alternatively comprise a transducer for emitting a surface acoustic wave into the cell construct. This may be used for sensing mass and mechanical properties of the cell construct.

The actuators may alternatively comprise electrodes for electroporation of cells. Thus, cell permeability may be allowed and selective introduction of molecular payloads may be provided.

The actuators need not necessarily be used in combination with sensing or measuring of a response from the cell construct. Rather, the actuators may affect, such as mechanically affect, the cell construct, e.g. for controlling culturing of cells, without a response being measured. Thus, the semiconductor cell culture device may comprise actuators in combination with sensors, but the semiconductor cell culture device may alternatively only comprise actuators or only comprise sensors.

When actuators and sensors are provided, actuators and sensors may be arranged on common island structures or may be arranged on separate island structures.

According to an embodiment, the mesh structure has a regular pattern forming an array of island structures and an array of through-pores.

Such a mesh structure may be easy to manufacture as identical structures are to be formed in a pattern. The regular pattern may be suitable for a three-dimensional cell culture as through-pores which may be needed for the cell culture may be evenly distributed over an entire cell culture portion.

Further, the regular pattern may ensure that sensors and/or actuators may be arranged in a regular pattern to provide an even distribution of sensors and/or actuators. This enables the semiconductor cell culture device to provide sensing/actuation throughout a cell culture at the cell culture portion.

According to an embodiment, the island structures may have a maximum dimension of at least 5 µm, wherein the bridge structures may have a width of at least 5 µm and a length of at least 10 µm, wherein the area of the cell culture portion has a maximum dimension of at least 500 µm, wherein a thickness of the cell culture portion is at least 1 µm and wherein a thickness of the supporting structure is at least 1 µm.

Island structures may have varying geometric shapes, e.g. circular, rectangular, polygonal, or arbitrarily shaped. The island structures within a cell culture device may have identical or varying geometric shape. A dimension of an island structure may be defined as a largest distance between two positions on sides of the island structure (e.g. length of rectangle, diameter of circle, maximum axis of arbitrary shape).

According to an embodiment, the island structures may have a maximum dimension of at least 5 µm, 10 µm, 25 µm, 50 µm, 100 µm or 200 µm. The maximum dimension of the island structures may be selected based on a size of e.g. sensors and/or actuators to be arranged on the island structures. Also, the maximum dimension of the island structures may be selected based on desired flexibility and stability of the mesh structure.

Neighboring island structures may be connected by bridge structures. Bridge structures may also have varying geometric shapes, e.g. to follow differently shaped paths, which may be identical or varying within a cell culture device. Typically, a bridge structure may comprise a constant width (size in the plane of the semiconductor material layer perpendicular to a path along the bridge structure between two island structures). The bridge structure may extend along a straight path between two island structures, but may alternatively for example extend along a circular spiral path or a serpentine path. The bridge structure may be defined by the width and the length of the bridge structure between the two island structures.

According to an embodiment, the bridge structures may have a width of at least 5 µm, 10 µm, 15 µm, or 25 µm. The width of the bridge structures may be selected based on ensuring that wires for connections to sensors and/or actuators on the island structures may be arranged on the bridge structures. Also, the width of the bridge structures may be selected based on desired flexibility and stability of the mesh structure.

According to an embodiment, the bridge structures may have a length at least corresponding to a distance between two island structures. The length of the bridge structures may be at least 10 µm, 50 µm, 100 µm or 200 µm. The length of the bridge structures may be selected based on a distance between two island structures. The length of the bridge structures may also be selected based on desired flexibility and stability of the mesh structure, e.g. if a serpentine path of the bridge structure is used.

Through-pores may be defined as a spacing surrounded by a plurality of island structures and a plurality of bridge structures interconnecting the island structures. A through-pore may have varying geometric shapes, e.g. circular, square, polygonal or arbitrarily shaped. The through-pores within a cell culture device may have identical or varying geometric shape. A dimension of a through-pore may be defined as a largest distance between two positions on structures surrounding the through-pore (e.g. diameter of circle, side of square, maximum axis of arbitrary shape).

According to an embodiment, the through-pores may have a maximum dimension of less than 1 µm, 5 µm, 10 µm, 50 µm, 90 µm. The maximum dimension of the through-pores may be selected for controlling transport through the through-pores, such as to select a desired permeability of the cell culture portion. For example, the through-pores may have a maximum dimension of no more than 10 µm, such that cell soma are unable to pass but cell media and/or cellular neurites may pass the through-pores. According to an embodiment, the through-pores may have a maximum dimension of approximately 80 µm or in a range of 80-100 µm. This may be advantageous in enabling three-dimensional growth of neuronal cell constructs. The dimensions of the through-pores may also be selected based on desired flexibility and stability of the mesh structure.

An area of the cell culture portion may define an overall size of the cell culture portion for the three-dimensional cell culture. A maximum dimension of the cell culture portion may be defined as a largest distance between two positions on periphery of the cell culture portion (e.g. length of rectangle, diameter of circle, maximum axis of arbitrary shape).

According to an embodiment, the cell culture portion may have a maximum dimension of at least and/or no more than 500 µm, 1 mm, 2 mm, 3 mm, 5 mm, 10 mm or 100 mm. The dimension of the cell culture portion may be selected based on a desired area in which sensing and/or actuation of the three-dimensional cell culture is desired. The dimension of the cell culture portion may also be selected based on desired flexibility and stability of the mesh structure.

A thickness of the cell culture portion may define a thickness of the semiconductor material layer in the area of the cell culture portion. The thickness may be constant or varying in the cell culture portion.

According to an embodiment, the thickness of the cell culture portion is at least and/or no more than 1 µm, 5 µm, 10 µm, 15 µm, 17 µm, or 25 µm. The thickness of the cell culture portion may be selected based on function of transport of cell constructs, cellular components, proteins or other large molecules through the cell culture portion. The thickness of the cell culture portion may also be selected based on desired flexibility and stability of the mesh structure.

A thickness of the supporting structure may define a thickness of the semiconductor material layer and/or a structure attached to the semiconductor material layer. The supporting structure may be solid in a relatively large area, such that the supporting structure may provide support to the cell culture portion, even though the supporting structure need not necessarily be thicker than the cell culture portion. The thickness of the supporting structure may thus be smaller than, equal to, or larger than the thickness of the cell culture portion.

According to an embodiment, the thickness of the supporting structure is at least 1 µm, 10 µm, 50 µm, 100 µm, 300 µm, 400 µm, 500 µm, or 725 µm. The thickness of the supporting structure may be selected so as to provide stability to the semiconductor cell culture device. The thickness of the supporting structure may also be selected in order to provide a desired compactness of the semiconductor cell culture device. The thickness of the supporting structure may also be selected to provide a desired distance between the cell culture portion and another structure, such as another cell culture portion of another semiconductor cell culture device in a stack of cell culture devices.

According to an embodiment, the supporting structure is configured to surround the area of the cell culture portion.

Hence, a support may be provided surrounding the cell culture portion, which may be useful in ensuring a stability of the cell culture portion in the entire area of the cell culture portion.

According to an embodiment, a thickness of the supporting structure is larger than a thickness of the cell culture portion.

This implies that the supporting structure may provide a stable support to the cell culture portion. The thickness of the supporting structure may also define a distance between the cell culture portion and another structure.

According to an embodiment, grooves extending perpendicularly to a plane defined by the semiconductor material layer are arranged on sidewalls of island structures and/or sidewalls of bridge structures.

Growth of cells may be stimulated along the grooves. Thus, by arranging grooves on sidewalls of island structures and/or sidewalls of bridge structures, growth of cells extending along the through-pores may be stimulated. The grooves may further facilitate alignment of cells along the through-pores.

According to an embodiment, the semiconductor cell culture device further comprises at least one aperture through the semiconductor material layer adjacent to the cell culture portion for allowing forming of a wall of a culture space through the semiconductor material layer to form the wall around the cell culture portion.

Thus, a culture space may be formed surrounding the cell culture portion and extending on opposite sides of the semiconductor material layer in which the cell culture portion is defined. This may be useful in defining a confined space in which the three-dimensional cell culture is formed.

The culture space may be formed with open ends on both sides of the semiconductor material layer forming a tubular space or with a closed end at one side forming a well.

The forming of the culture space may be achieved e.g. through casting or injection molding of the wall through the at least one aperture.

The at least one aperture may comprise one aperture extending to enclose almost entirely the cell culture portion. However, in order to provide a strong connection between the semiconductor material layer on opposite sides of the at least one aperture, the semiconductor cell culture device may comprise a plurality of apertures, such that connections between the apertures for connecting the semiconductor material layer on opposite sides of the at least one aperture may be distributed along a circumference enclosing the cell culture portion. The at least one aperture may then have an arc shape.

According to an embodiment, the semiconductor cell culture device further comprises one or more apertures within or adjacent to the area of the cell culture portion, wherein the one or more apertures are configured for providing fluid flow to the cell construct.

Thus, the through-pores of the mesh structure may be used for providing a structure through which a cell construct may grow. This may be combined with the one or more apertures for providing flow of culture media or other fluids through the cell culture portion.

The one or more apertures may be of varying size. By selecting the size of the one or more apertures, fluid velocity and/or selective permeability of the apertures may be tuned.

The one or more apertures may be arranged within the mesh structure or adjacent to the mesh structure. For instance, the one or more apertures may be arranged inside an area defined by a wall of a culture space that may be formed through the semiconductor material layer.

According to a second aspect, there is provided a system for three-dimensional cell culture, comprising a plurality of semiconductor cell culture devices according to the first aspect, wherein the semiconductor cell culture devices are stacked such that the cell culture portion of a first semiconductor cell culture device of the plurality of semiconductor cell culture devices is arranged above a second semiconductor cell culture device of the plurality of semiconductor cell culture devices.

Effects and features of this second aspect are largely analogous to those described above in connection with the first aspect. Embodiments mentioned in relation to the first aspect are largely compatible with the second aspect.

Thanks to stacking of semiconductor cell culture devices, several planes through a three-dimensional cell culture may be defined. This may be useful in controlling growth of a three-dimensional cell culture. Further, if the semiconductor cell culture devices are provided with sensors and/or actuators, sensing and/or actuation of the three-dimensional cell culture may be provided in several planes extending through the three-dimensional cell culture.

According to an embodiment, the semiconductor cell culture devices are stacked by the supporting structure of the first semiconductor cell culture device being arranged on the supporting structure of the second cell culture device such that a distance is provided between the cell culture portion of the first semiconductor cell culture device and the cell culture portion of the second semiconductor cell culture device.

Thus, the supporting structures of the semiconductor cell culture devices may be used for defining distances between the cell culture portions. It should be realized that the supporting structure of the first semiconductor cell culture device being arranged on the supporting structure of the second semiconductor cell culture device does not necessarily imply that the supporting structure of the first semiconductor cell culture device is directly on the supporting structure of the second semiconductor cell culture device. Rather, one or more other layers may be arranged therebetween.

According to an embodiment, the semiconductor cell culture devices comprise electrodes on the island structures and wherein connections to the electrodes are provided through independent bond pads of each of the semiconductor cell culture devices.

Hence, electronic circuitry (sensors and/or actuators) on each semiconductor cell culture device may be independently connected to external circuitry. The external circuitry may be provided in form of a printed circuit board that may provide circuitry for controlling sensors and/or actuators and/or for read-out and processing of information acquired by the sensors.

According to another embodiment, the semiconductor cell culture devices comprise electrodes on island structures and wherein a first semiconductor cell culture device is wire bonded to a second semiconductor cell culture device which is connected to external circuitry for connecting the electrodes on the first semiconductor cell culture device to the external circuitry. Thus, connections between an external circuitry and the semiconductor cell culture devices may be shared.

According to another embodiment, the semiconductor cell culture devices comprise electrodes on the island structures and wherein a through-substrate via is provided in at least one of the semiconductor cell culture devices for electrically connecting the semiconductor cell culture device to another semiconductor cell culture device for sharing a bond pad.

In this embodiment, it is required to form connections between the layers of different semiconductor cell culture devices. However, then it may be sufficient to connect the semiconductor cell culture devices through a single bond pad to external circuitry.

BRIEF DESCRIPTION OF THE DRAWINGS

The above, as well as additional objects, features and advantages of the present inventive concept, will be better understood through the following illustrative and non-limiting detailed description, with reference to the appended drawings. In the drawings like reference numerals will be used for like elements unless stated otherwise.

FIGS. 3a-d are schematic views illustrating different embodiments of mesh structures.

FIG. 4 is a schematic view of a detail of a mesh structure.

DETAILED DESCRIPTION

Figure 1:
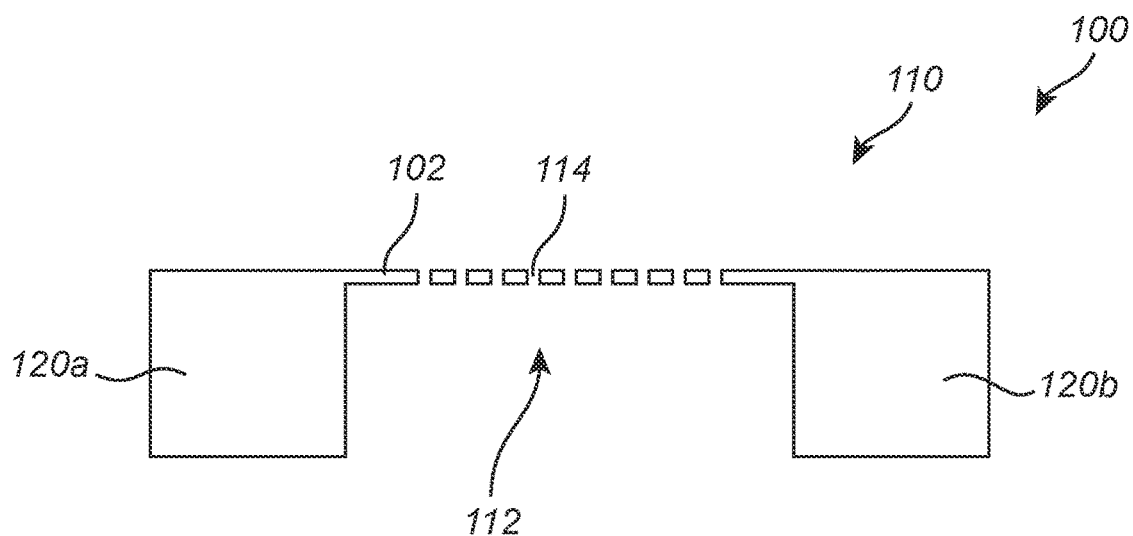
FIG. 1 is a schematic cross-sectional view of a semiconductor cell culture device according to an embodiment.

Referring now to FIG. 1, a semiconductor cell culture device 100 according to an embodiment will be described. The semiconductor cell culture device 100 comprises a cell culture portion 110 in a layer 102 of semiconductor material. The cell culture portion 110 comprises a mesh structure 112, having through-pores 114 allowing for selective transport of cell constructs, cellular components, proteins or other large molecules through the layer 102. Thanks to the through-pores 114, the semiconductor cell culture device 100 may be used for three-dimensional cell culture, wherein the cell culture portion 110 extends within the interior of a cell construct.

The semiconductor cell culture device 100 may be used for growth of three-dimensional cell cultures. For instance, the mesh structure 112 of the semiconductor cell culture device 100 may have a particular shape and/or may have particular dimensions of the through-pores 114 such that the three-dimensional cell culture may be controlled. Therefore, the semiconductor cell culture device 100 may be useful as such for three-dimensional cell culture.

Thanks to forming the cell culture portion 110 and mesh structure 112 in a semiconductor material, the mesh structure 112 may be formed with accurate control of minute structures using semiconductor manufacturing technology. For instance, the layer 102 of semiconductor material may be a silicon layer, such as using a silicon wafer.

Further, thanks to defining the cell culture portion 110 with the mesh structure 112 in a semiconductor material, the semiconductor cell culture device 100 facilitates providing sensors and/or actuators in the mesh structure 112 such that sensors and/or actuators extending into the interior of a three-dimensional cell culture may be provided. Hereinafter, the semiconductor cell culture device 100 will be described mainly in relation to having sensors and/or actuators arranged in the mesh structure 112.

The semiconductor cell culture device 100 may further comprise a supporting structure 120. The supporting structure 120 may be formed as a solid portion of the layer 102 of the semiconductor material so as to provide support for the cell culture portion 110 and the mesh structure 112. The supporting structure 120 may alternatively or additionally be formed by a structure being attached to the layer 102 of the semiconductor material. The mesh structure 112 may, by means of the through-pores 114, be highly flexible and may need the supporting structure 120 as support of the highly flexible surface.

As shown in FIG. 1, the supporting structure 120 may have a first portion 120a and a second portion 120b, arranged at different sides of an area of the cell culture portion 110 in the layer 102 of semiconductor material. The supporting structure 120 may be formed by a portion of the layer 102 having a larger thickness than a thickness of the cell culture portion 110, even though it should be understood that the thickness of the supporting structure 120 may be equal to or even less than the thickness of the cell culture portion 110.

Figure 2:
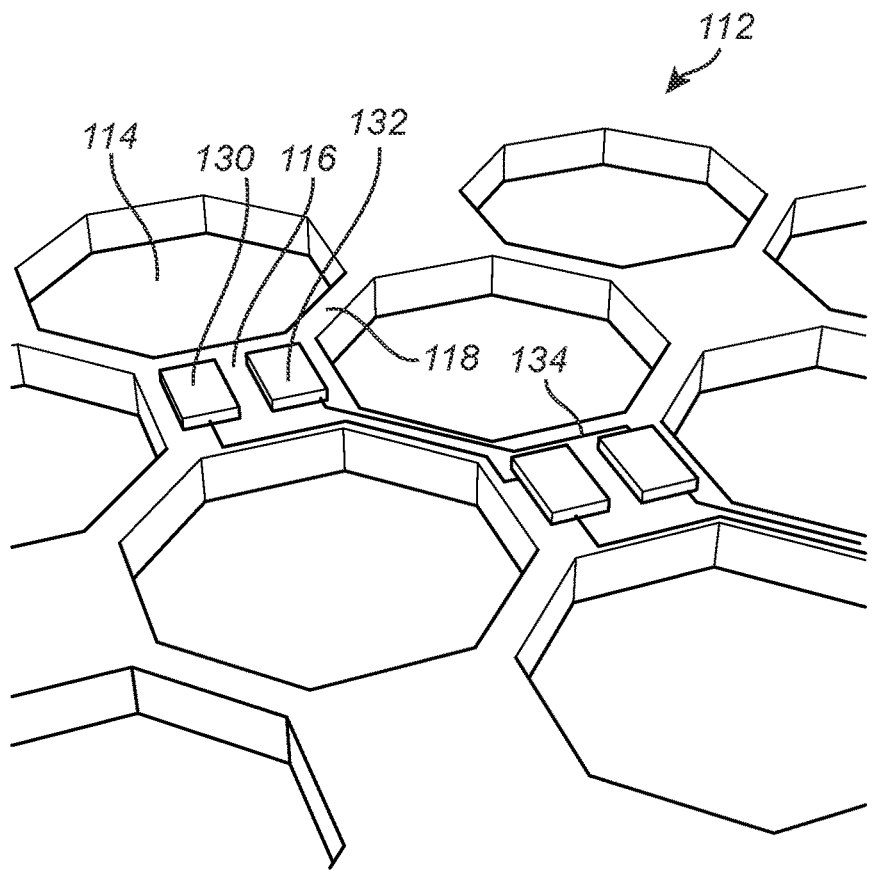
FIG. 2 is a schematic view illustrating a mesh structure of a semiconductor cell culture device.

Referring now to FIG. 2, the mesh structure 112 according to an embodiment will be described in further detail.

The mesh structure 112 may comprise island structures 116 interconnected by bridge structures 118. The island structures 116 and the bridge structures 118 are formed in the layer 102 of semiconductor material. The island structures 116 may together with the bridge structures 118 surround through-pores 114 and therefore define dimensions of the through-pores 114.

The island structures 116, bridge structures 118 and through-pores 114 there-between may be formed in many different shapes and dimensions. For instance, size and shapes of the through-pores 114, the island structures 116, and the bridge structures 118 may be designed in relation to selective permeability of the mesh structure 112 (i.e. which type of substances, cells, or cellular components should be allowed to pass the mesh structure 112), and desired stability and flexibility of the mesh structure 112.

The mesh structure 112 may provide a regular pattern, wherein the through-pores 114, island structures 116, and bridge structures 118 are evenly distributed within the mesh structure 112. This may provide a regular arrangement of sensors 130 and/or actuators 132 on the island structures 116. However, the mesh structure 112 may alternatively have different sizes of the structures in different portions of the mesh structure 112.

The semiconductor cell culture device 100 may be provided with sensors 130 and/or actuators 132 arranged on the island structures 116. These sensors 130 and/or actuators 132 may include various types. The mesh structure 112 may further provide connections 134 to the sensors 130 and/or actuators 132 arranged on the bridge structures 116 so as to allow control from and/or transfer of signals to circuitry arranged external to the mesh structure 112. The connections 134 may comprise wires for transferring electrical signals, but may in some embodiments also or alternatively comprise waveguides for transferring an electromagnetic wave, such as light.

The sensors 130 may include electrodes for detecting electrical signals. Thus, electrical signals propagating in the three-dimensional cell culture, spontaneously or as a response to stimulation, may be recorded.

The sensors 130 may include photosensitive areas. This may be used for imaging an interior of the cell construct.

The sensors 130 may include a piezoelectric sensor. This may be used for detecting e.g. changes in pressure, temperature or strain within the cell construct.

The actuators 132 may include active electrodes for providing a stimulation signal to the cell construct.

The actuators 132 may include a light source for illuminating the cell construct. The light source may be arranged at the island structure 116. Alternatively, the cell construct may be illuminated by the actuator 132 including a light output coupler from a waveguide that transfers light to the island structure 116.

The actuators 132 may include a transducer for emitting a surface acoustic wave into the cell construct. This may be used for sensing mass and mechanical properties of the cell construct.

Referring now to FIGS. 3a-d, some alternative embodiments of mesh structures 112 are illustrated. It should be realized that the mesh structure 112 may be further designed in various other ways.

FIG. 3a illustrates the same structure as shown in FIG. 2, wherein the mesh structure 112 has square-shaped island structures 116 with straight bridge structures 118. Each island structure 116 is connected to four neighboring island structures 116.

FIG. 3b illustrates hexagonal island structures 116 with straight bridge structures 118, wherein each island structure 116 is connected to six neighboring island structures 116.

FIG. 3c illustrates a centrally arranged island structure 116 being connected to a circular spiral path defined by the bridge structure 118. The bridge structure 118 allows a flexibility for transforming the shape of the mesh structure 112.

FIG. 3d illustrates a centrally arranged island structure 116 connected to a serpentine shaped path defined by the bridge structure 118. The bridge structure 118 also allows a flexibility for transforming the shape of the mesh structure 112.

Referring now to FIG. 4, shapes of sidewalls of island structures 116 and bridge structures 118 are illustrated. The sidewalls may be provided with grooves 119 that extend perpendicularly to the plane of the layer 102 of semiconductor material. Thus, the grooves 119 may extend along a direction of through-pores 114.

The grooves 119 may facilitate cellular alignment along the grooves 119 which may be useful in ensuring a desired cell growth in the cell culture portion 112.

The sidewalls may be straight such that a cross-section of the through-pores 114 may be constant through the thickness of the layer 102 of semiconductor material. However, the sidewalls may alternatively be sloped such that the through-pores 114 may have an increasing or decreasing size of the cross-section through the thickness of the layer 102.

Figure 5:
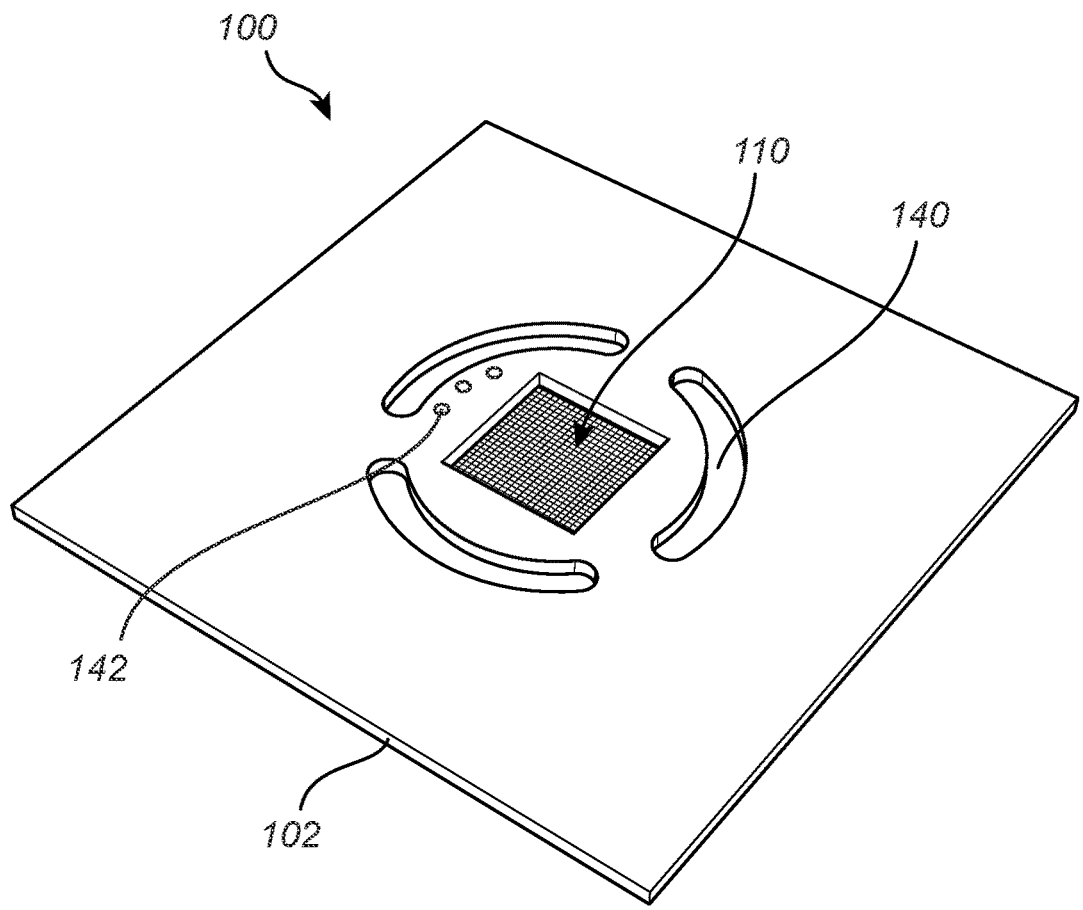
FIG. 5 is a schematic perspective view of a semiconductor cell culture device according to an embodiment.

Referring now to FIG. 5, further structures may be formed in the layer 102 of semiconductor material. As illustrated in FIG. 5, the semiconductor cell culture device 100 may comprise a plurality of arc-shaped apertures 140. The arc-shaped apertures 140 may be used for forming a wall of a culture space through the semiconductor material. Thus, the semiconductor cell culture device 100 facilitates forming a wall around the cell culture portion 110 to form e.g. a tubing or a well in which cell culture may take place.

The arc-shaped apertures 140 may be configured to substantially enclose the cell culture portion 110 to facilitate that a wall of the culture space is formed enclosing the cell culture portion 110 therein. However, the arc-shaped apertures 140 may still provide a connection in the semiconductor material on opposite sides of the apertures 140 between the cell culture portion 110 and semiconductor material that will be arranged outside the culture space. This ensures stability of the shape of the semiconductor cell culture device 100 before the wall of the culture space is formed. In order to facilitate a stability of the shape of the device 100, a plurality of arc-shaped apertures 140 are preferably provided.

It should be realized that the apertures 140 may have another shape depending on a desired cross-sectional shape of the culture space.

The wall may be formed through the layer 102 of semiconductor material, e.g. by a castable or injectable material being molded through the apertures 140.

As further illustrated in FIG. 5, the semiconductor cell culture device 100 may further comprise one or more fluid-flow apertures 142 through the layer 102 of semiconductor material. The fluid-flow apertures 142 may be arranged within the mesh structure 112 as particular apertures 142 which may have different shape or otherwise different properties than the through-pores 114. The fluid-flow apertures 142 may alternatively or additionally be arranged adjacent to the mesh structure 112, e.g. within an area enclosed by a wall of the culture space.

The one or more fluid-flow apertures 142 may provide flow of culture media or other fluids through the layer 102 of semiconductor material.

The one or more fluid-flow apertures 142 may be of varying size. By selecting the size of the one or more fluid-flow apertures 142, fluid velocity and/or selective permeability of the fluid-flow apertures 142 may be tuned.

Figure 6:
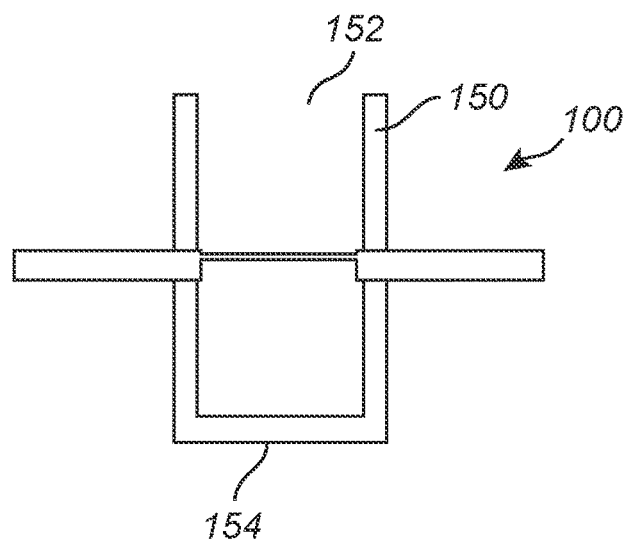
FIG. 6 is a schematic view illustrating use of a semiconductor cell culture device within a culture space.

Referring now to FIG. 6, the semiconductor cell culture device 100 is illustrated with a culture well 150 having an open end 152 at a first end above the cell culture portion 110 and a closed end 154 at a second end below the cell culture portion 110.

The culture well 150 may define a confined space in which cell culture takes place. The cell culture portion 110 is configured to extend through the confined space and thus enables sensing and/or actuation of interior of a cell construct that is cultured in the culture well 150.

Referring now to FIGS. 7a-d, a method of manufacturing of a semiconductor cell culture device 100 will be briefly discussed. The method should serve to illustrate one way of manufacturing the semiconductor cell culture device 100, and it should be realized that the semiconductor cell culture device 100 may be manufactured in different manners as will be appreciated by a person skilled in the art.

Figure 7A:
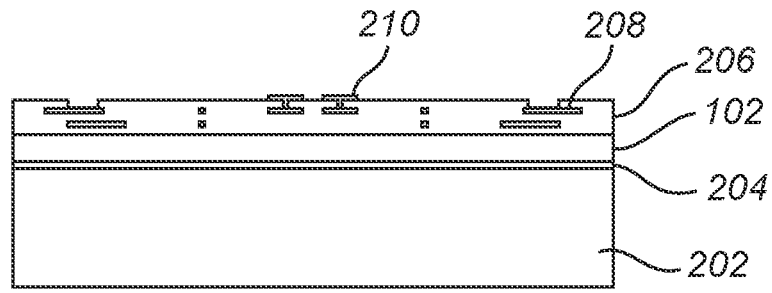
FIGS. 7a-d are schematic views illustrating manufacture of a semiconductor cell culture device.

As illustrated in FIG. 7a, the semiconductor cell culture device 100 may be formed as a silicon on insulator structure.

Hence, a semiconductor substrate 202, e.g. silicon, may be provided with a dielectric layer 204, e.g. SiO$_2$.

First, a layer 102 of semiconductor material may be formed on the dielectric layer 204. The thickness of the layer 102 may be selected in dependence of a desired thickness of the cell culture portion 110.

Then, dielectric layers 206 with metal patterns 208 and connections between different metal layers may be formed on the layer 102. Electrodes 210 may also be formed on a top surface.

Figure 7B:
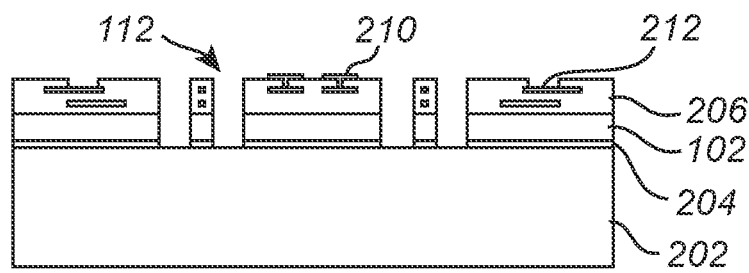

As illustrated in FIG. 7b, removing of dielectric material to form connections to bond pads 212 may then be performed. Then, selective removal of material may be performed to form a mesh structure 112 through the dielectric layers 206, the semiconductor layer 102 and the dielectric layer 204, e.g. by deep silicon etching from a front side of the device. Hence, the mesh structure 112 may be defined on the semiconductor substrate 202.

Figure 7C:
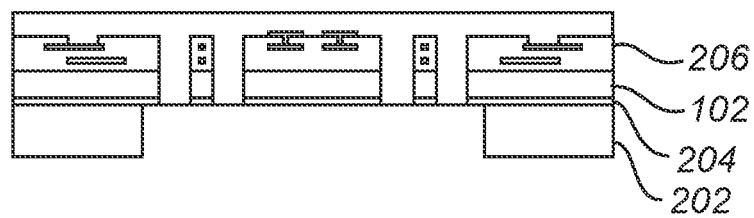

As illustrated in FIG. 7c, a sacrificial material may then be deposited extending into the mesh structure 112. Then, the semiconductor substrate 202 may be removed at least in the area of the cell culture portion 110. The semiconductor substrate 202 may be removed from a back side of the device, e.g. by first generally thinning the entire semiconductor substrate 202, e.g. stopping at a desired thickness of the supporting structure 120. Then, the semiconductor substrate material may be selectively removed in the area of the cell culture portion, e.g. by deep silicon etching.

Figure 7D:
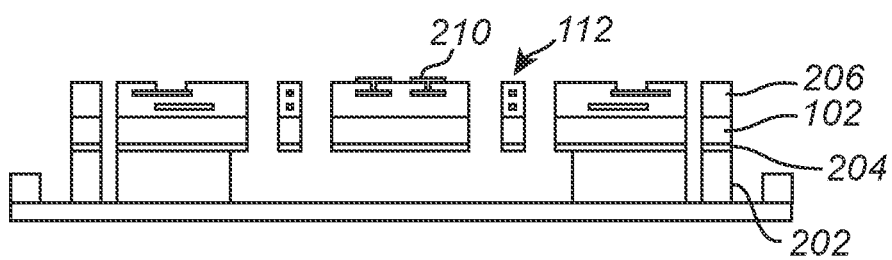

Finally, as illustrated in FIG. 7d, the sacrificial material may be removed and the structure may be attached to a dicing tape for dicing and packaging.

In an embodiment, the semiconductor cell culture device 100 is provided with electrodes 210. The electrodes 210 may for instance be passive electrodes.

The semiconductor cell culture device 100 may be provided with 1, 2 or more electrodes 210 per island structure 116.

The electrodes 210 may be of varying sizes and shapes. For instance, the electrodes 210 may be square, circular or arbitrarily shaped having a maximum dimension of 5 µm, 10 µm, 20 µm, 25 µm or 50 µm. The electrodes 210 may for instance be formed by tungsten, platinum, platinum-iridium alloys, iridium oxide, titanium nitride and/or poly(ethylenedioxythiophene) (PEDOT).

The connections to the electrodes 210 may be formed by wires or traces extending on the bridge structures 118. For instance, 1, 2 or more connections may be formed on a bridge structure 118. The connections may for instance be formed by copper, aluminum, or gold and may be formed in varying sizes and shapes.

Portions of electrodes 210 and connections may need to be insulated from the cell culture. Insulation may be achieved by a passivation layer being added, such as a layer of silicon nitride, silicon dioxide and/or insulating resists.

The semiconductor cell culture device 100 may further be provided with reference electrodes. Reference electrodes may be provided in the mesh structure 112, such as having a plurality of reference electrodes arranged in the mesh structure 112, e.g. on selected island structures 116.

Alternatively, reference electrodes may be provided adjacent to the cell culture portion 110 within the culture space 150. As a further alternative, reference electrodes may be arranged externally to the semiconductor cell culture device 100 and may be connected to external circuitry to which the semiconductor cell culture device 100 is also connected.

Figure 8:
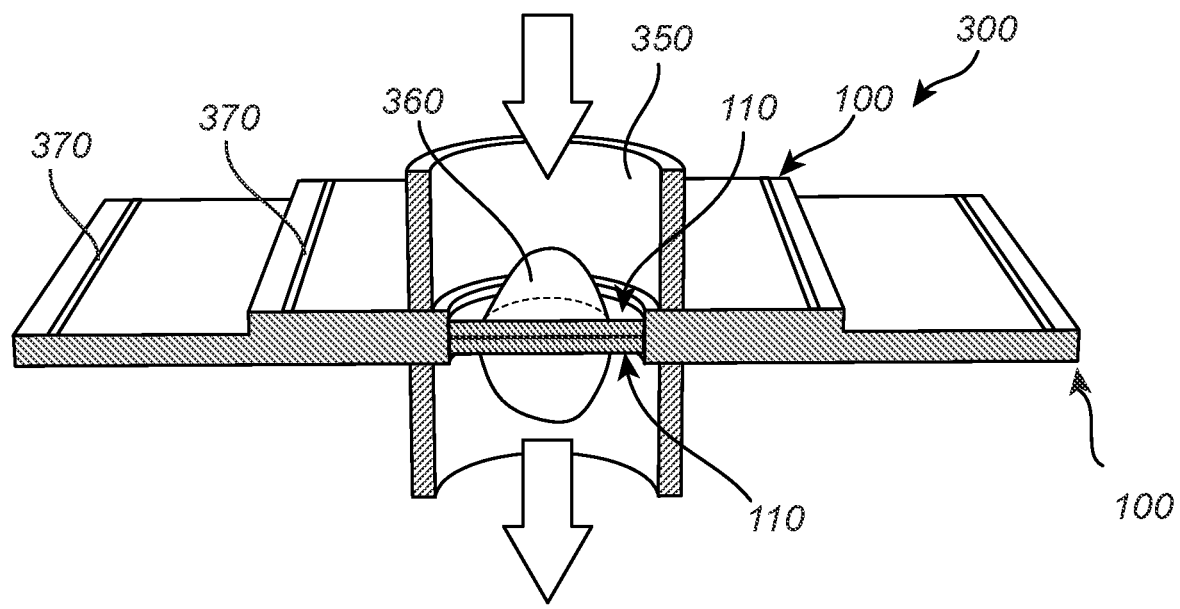
FIG. 8 is a schematic view illustrating a system comprising a plurality of semiconductor cell culture devices according to an embodiment.

Referring now to FIG. 8, a system 300 for three-dimensional cell culture will be described.

As illustrated in FIG. 8, a plurality of semiconductor cell culture devices 100 may be stacked on top of each other. A wall of a culture space 350 may be formed through all of the semiconductor cell culture devices 100 to define a culture space extending through all the cell culture portions 110. This implies that a plurality of cell culture portions 110 extending through different planes of the culture space 350 may be provided.

Thus, the system 300 may provide sensing and/or actuation distributed in three dimensions extending through the interior of a cell construct 360. Hence, the system 300 enables detailed information relating to three-dimensional cell constructs 360 to be acquired.

The semiconductor cell culture devices 100 may be stacked by the supporting structures 120 being arranged on top of each other.

When several semiconductor cell culture devices 100 are stacked such that fluid is allowed to flow across all layers defined by the semiconductor cell culture devices 100, a conformable layer may be arranged between the semiconductor cell culture devices 100.

The semiconductor cell culture devices 100 may for instance be integrated by direct silicon-silicon bonding, by means of a polydimethylsiloxane (PDMS) membrane, a bio-compatible silicone, a bio-compatible epoxy or biocompatible double-sided adhesive.

Each semiconductor cell culture device 100 may have independent contacts 370 to external circuitry, e.g. in the form of bond pads. The semiconductor cell culture devices 100 may thus comprise self-contained sensors 130 and/or actuators 132 with associated connections and may be independently bonded to e.g. an external printed circuit board.

However, according to an alternative, the semiconductor cell culture devices 100 may be provided with electrical interconnections. For instance, through-substrate vias may be provided for electrically integrating the semiconductor cell culture devices 100. Then, the semiconductor cell culture devices 100 may share a common bond pad which may be connected to external circuitry, e.g. an external printed circuit board.

According to yet another alternative, the semiconductor cell culture devices 100 may be wire bonded to each other in the stack such that a first semiconductor cell culture device may be wire bonded to a second semiconductor cell culture device which may in turn be wire bonded to a third semiconductor cell culture device and so forth until one semiconductor cell culture device is connected to the external circuitry.

The semiconductor cell culture devices 100 may have contacts 370 for connection to external circuitry arranged outside the culture space 350. Thus, connections from the mesh structure 112 may be routed to outside the culture space 350 and the contacts 370 may be arranged outside the culture space 350 in which fluid flow is provided.

Figure 9:
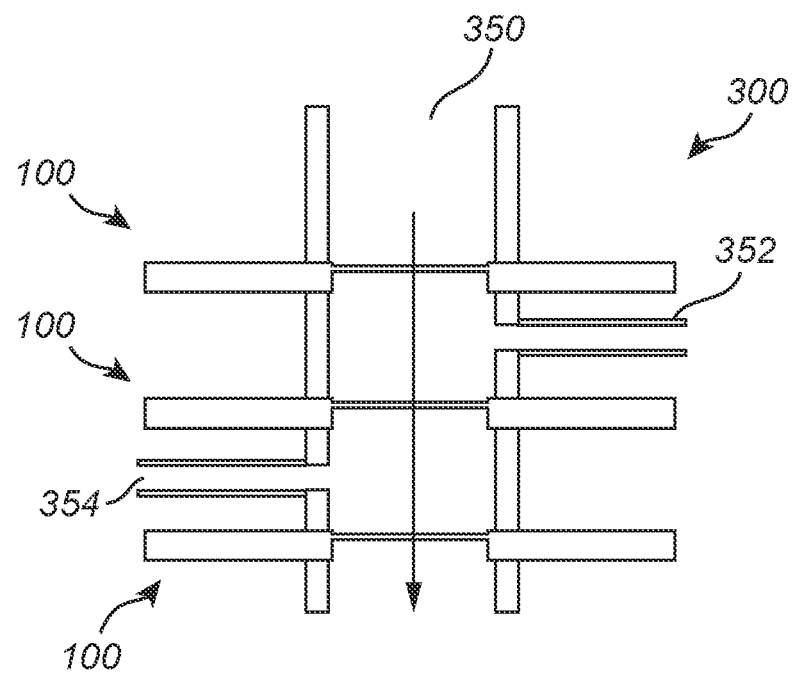
FIG. 9 is a schematic view of the system according to another embodiment.

Referring now to FIG. 9, an alternative embodiment of the system 300 is shown. As illustrated in FIG. 9, the culture space 350 may be provided with additional inlets 352 and/or outlets 354 between the semiconductor cell culture devices 100. Thus, additional fluid flow into or out of portions of the culture space 350 between the semiconductor cell culture devices 100 may be provided.

Referring now to FIGS. 10-13, some additional variations of the semiconductor cell culture device 100 and the system 300 will be illustrated and discussed.

Figure 10:
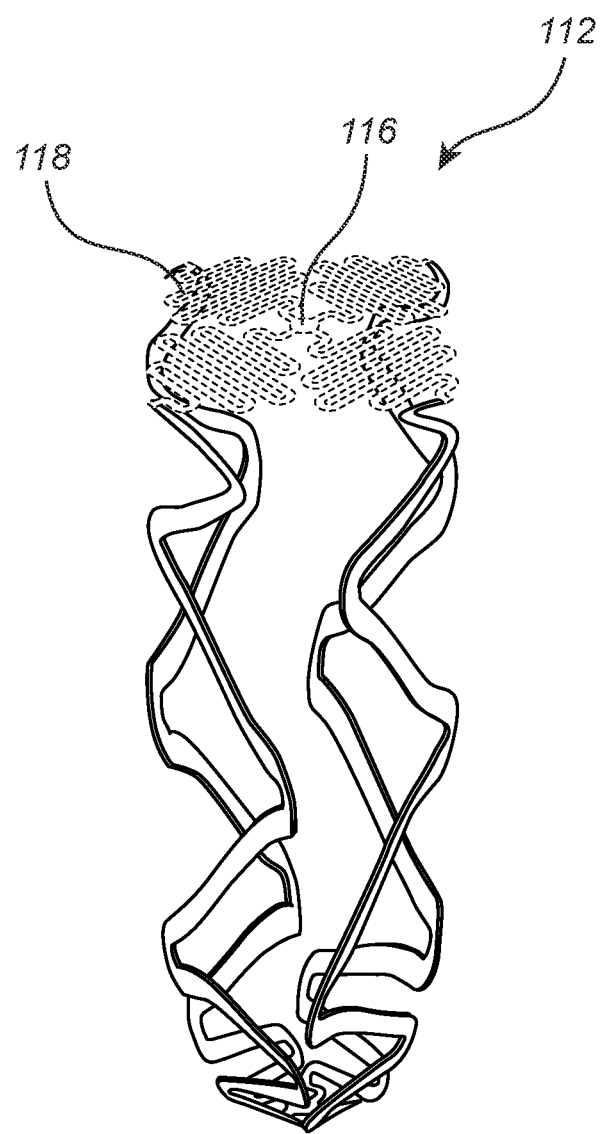
FIG. 10 is a schematic view illustrating an embodiment of the mesh structure.

In FIG. 10, an example of a highly compliant mesh structure 112 is illustrated. This may be beneficial in particular applications of cell culture.

The island structure 116 and bridge structures 118 illustrated in FIG. 10 are designed to an effective stiffness of approximately 6 kPa, which is on the same order of magnitude of stiffness of brain tissue.

Figure 11:
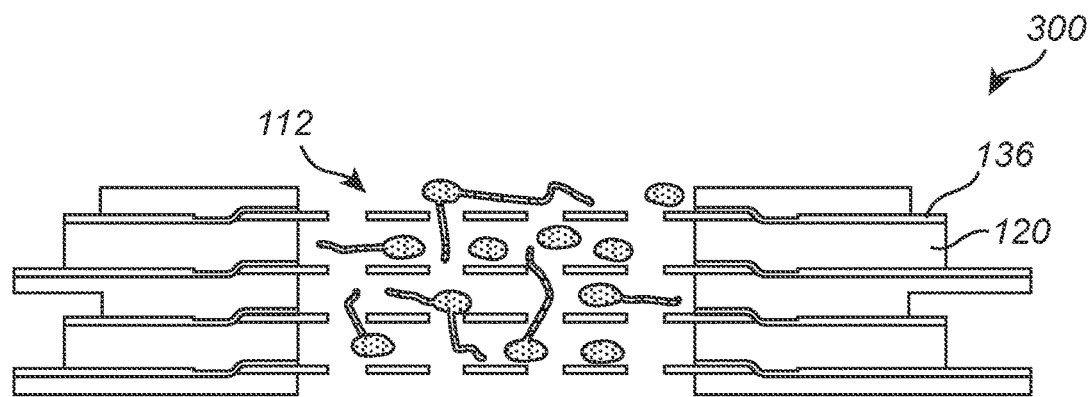
FIG. 11 is a schematic view of the system according to another embodiment.

Referring now to FIG. 11, the supporting structure 120 is formed by a thin flexible material. For instance, a thin organic flexible material such as polyimide may be used.

The mesh structures 112 may be connected at sides of the mesh structure to the flexible material for providing the supporting structure 120. Further, electrical connections to the mesh structures 112 may be provided by means of conductors 136 provided on a surface of the flexible material.

The conductors 136 may be patterned on the mesh structure 112 being connected on the surface of the flexible material. The conductors 136 may be provided with an open end to allow further connection to e.g. a wire bond.

The use of the thin flexible material may allow mesh structures 112 to be packed very closely together, such as spaced apart by 20-50 μm. This allows for high resolution of sensors 130 and/or actuators 132 in a direction perpendicular to the mesh structure 112.

Stacking of the supporting structures 120 of flexible material may be provided by gluing or clamping supporting structures 120 together.

Figure 12:
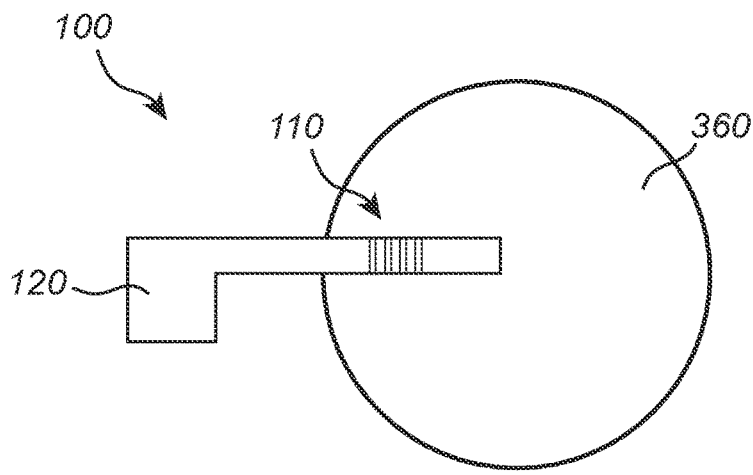
FIG. 12 is a schematic view of the semiconductor cell culture device according to another embodiment.

Referring now to FIG. 12, the semiconductor cell culture device 100 may be provided with a supporting structure 120 only at one side of an area of the cell culture portion 112. Instead of defining a culture space in which the cell culture portion 112 is arranged, the cell culture portion 112 may extend from the supporting structure 120 in a cantilever-type arrangement to extend into a three-dimensional cell culture 360.

The three-dimensional cell culture 360 may extend on opposite sides of the cell culture portion 110 but may also extend to surround an end of the layer 102 of semiconductor material layer.

The cell culture portion 110 may thus probe into the three-dimensional cell culture, which may be used for analysis into interior of cell constructs, without the cell constructs necessarily being confined in a particular culture space.

A plurality of probes may be used in different positions in relation to a three-dimensional cell culture for enabling sensing and/or actuation in three dimensions.

Figure 13:
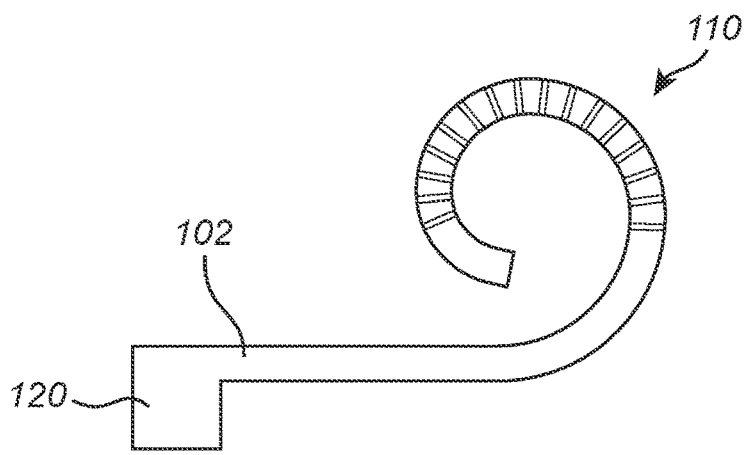
FIG. 13 is a schematic view of the semiconductor cell culture device according to another embodiment.

Referring now to FIG. 13, the semiconductor cell culture device 100 may be configured such that the layer 102 of semiconductor material does not necessarily extend in a plane. Rather, the layer 102 may be transformed into another desired shape extending in three dimensions, which may be used e.g. for stimulating a particular growth of a cell construct. Thus, the cell culture portion 110 may extend in three dimensions.

For instance, as illustrated in FIG. 13, the layer 102 may assume a helical shape, which may be useful in controlling a desired shape of a cell construct.

In the above the inventive concept has mainly been described with reference to a limited number of examples. However, as is readily appreciated by a person skilled in the art, other examples than the ones disclosed above are equally possible within the scope of the inventive concept, as defined by the appended claims.

The invention claimed is:

1. A semiconductor cell culture device for three-dimensional cell culture, said device comprising:

a semiconductor material layer in which a cell culture portion of semiconductor material is defined, wherein the cell culture portion defines an area within the semiconductor material layer surrounded by semiconductor material, wherein the cell culture portion comprises a mesh structure having island structures being interconnected by bridge structures and defining through-pores between the island structures allowing for selective transport of cell constructs, cellular components, proteins or other large molecules through the semiconductor material layer and on opposite sides of the cell culture portion in the semiconductor material layer;

a supporting structure connected to the cell culture portion; and a plurality of actuators for affecting a cell construct, wherein each of the plurality of actuators is arranged on an island structure and wherein actuator connections to the plurality of actuators are arranged on the bridge structures.

2. The semiconductor cell culture device according to claim 1, further comprising a plurality of sensors for analysis of a cell construct, wherein each of the plurality of sensors is arranged on an island structure and wherein sensor connections to the plurality of sensors are arranged on the bridge structures.

3. The semiconductor cell culture device according to claim 2, wherein the plurality of sensors comprises at least one of: an electrode for detecting an electrical signal, a photosensitive area for detecting light or a piezoelectric sensor.

4. The semiconductor cell culture device according to claim 1, wherein the mesh structure has a regular pattern forming an array of island structures and an array of through-pores.

5. The semiconductor cell culture device according to claim 1, wherein the island structures may have a maximum dimension of at least 5 μm, wherein the bridge structures may have a width of at least 5 μm and a length of at least 10 μm, wherein the area of the cell culture portion has a maximum dimension of at least 500 μm, wherein a thickness of the cell culture portion is at least 1 μm and wherein a thickness of the supporting structure is at least 1 μm.

6. The semiconductor cell culture device according to claim 1, wherein the supporting structure is configured to surround the area of the cell culture portion.

7. The semiconductor cell culture device according to claim 1, wherein a thickness of the supporting structure is larger than a thickness of the cell culture portion.

8. The semiconductor cell culture device according to claim 1, wherein grooves extending perpendicularly to a plane defined by the semiconductor material layer are arranged on sidewalls of island structures and/or sidewalls of bridge structures.

9. The semiconductor cell culture device according to claim 1, further comprising at least one aperture through the semiconductor material layer adjacent to the cell culture portion for allowing forming of wall of a culture space through the semiconductor material layer to form the wall around the cell culture portion.

10. The semiconductor cell culture device according to claim 1, further comprising one or more apertures within or adjacent to the area of the cell culture portion, wherein the one or more apertures are configured for providing fluid flow to the cell construct.

11. A system for three-dimensional cell culture, comprising a plurality of semiconductor cell culture devices, wherein each semiconductor cell culture device comprises:
a semiconductor material layer in which a cell culture portion of semiconductor material is defined, wherein the cell culture portion defines an area within the semiconductor material layer surrounded by semiconductor material, wherein the cell culture portion comprises a mesh structure having island structures being interconnected by bridge structures and defining through-pores between the island structures allowing for selective transport of cell constructs, cellular components, proteins or other large molecules through the semiconductor material layer and on opposite sides of the cell culture portion in the semiconductor material layer; and
a supporting structure connected to the cell culture portion, wherein the semiconductor cell culture devices are stacked such that the cell culture portion of a first semiconductor cell culture device of the plurality of semiconductor cell culture devices is arranged above a second semiconductor cell culture device of the plurality of semiconductor cell culture devices.

12. The system according to claim 11, wherein the semiconductor cell culture devices are stacked by the supporting structure of the first semiconductor cell culture device being arranged on the supporting structure of the second semiconductor cell culture device such that a distance is provided between the cell culture portion of the first semiconductor cell culture device and the cell culture portion of the second semiconductor cell culture device.

13. The system according to claim 11, wherein the semiconductor cell culture devices comprise electrodes on the island structures and wherein connections to the electrodes are provided through independent bond pads of each of the semiconductor cell culture devices.

14. The system according to claim 11, wherein the semiconductor cell culture devices comprise electrodes on the island structures and wherein a through-substrate via is provided in at least one of the semiconductor cell culture devices for electrically connecting the semiconductor cell culture device to another semiconductor cell culture device for sharing a bond pad.

15. A semiconductor cell culture device for three-dimensional cell culture, said device comprising:
a semiconductor material layer in which a cell culture portion of semiconductor material is defined, wherein the cell culture portion defines an area within the semiconductor material layer surrounded by semiconductor material, wherein the cell culture portion comprises a mesh structure having island structures being interconnected by bridge structures and defining through-pores between the island structures allowing for selective transport of cell constructs, cellular components, proteins or other large molecules through the semiconductor material layer and on opposite sides of the cell culture portion in the semiconductor material layer; and
a supporting structure connected to the cell culture portion,
wherein the island structures may have a maximum dimension of at least 5 µm, wherein the bridge structures may have a width of at least 5 µm and a length of at least 10 µm, wherein the area of the cell culture portion has a maximum dimension of at least 500 µm, wherein a thickness of the cell culture portion is at least 1 µm and wherein a thickness of the supporting structure is at least 1 µm.

16. A semiconductor cell culture device for three-dimensional cell culture, said device comprising:
a semiconductor material layer in which a cell culture portion of semiconductor material is defined, wherein the cell culture portion defines an area within the semiconductor material layer surrounded by semiconductor material, wherein the cell culture portion comprises a mesh structure having island structures being interconnected by bridge structures and defining through-pores between the island structures allowing for selective transport of cell constructs, cellular components, proteins or other large molecules through the semiconductor material layer and on opposite sides of the cell culture portion in the semiconductor material layer; and
a supporting structure connected to the cell culture portion,
wherein grooves extending perpendicularly to a plane defined by the semiconductor material layer are arranged on sidewalls of island structures and/or sidewalls of bridge structures.

17. A semiconductor cell culture device for three-dimensional cell culture, said device comprising:
a semiconductor material layer in which a cell culture portion of semiconductor material is defined, wherein the cell culture portion defines an area within the semiconductor material layer surrounded by semiconductor material, wherein the cell culture portion comprises a mesh structure having island structures being interconnected by bridge structures and defining through-pores between the island structures allowing for selective transport of cell constructs, cellular components, proteins or other large molecules through the semiconductor material layer and on opposite sides of the cell culture portion in the semiconductor material layer;
a supporting structure connected to the cell culture portion; and
at least one aperture through the semiconductor material layer adjacent to the cell culture portion for allowing forming of wall of a culture space through the semiconductor material layer to form the wall around the cell culture portion.

18. A semiconductor cell culture device for three-dimensional cell culture, said device comprising:
a semiconductor material layer in which a cell culture portion of semiconductor material is defined, wherein the cell culture portion defines an area within the semiconductor material layer surrounded by semiconductor material, wherein the cell culture portion comprises a mesh structure having island structures being interconnected by bridge structures and defining through-pores between the island structures allowing for selective transport of cell constructs, cellular components, proteins or other large molecules through the semiconductor material layer and on opposite sides of the cell culture portion in the semiconductor material layer;
a supporting structure connected to the cell culture portion; and
one or more apertures within or adjacent to the area of the cell culture portion, wherein the one or more apertures are configured for providing fluid flow to the cell construct.

* * * * *